US009687390B2

(12) United States Patent
Davidson et al.

(10) Patent No.: US 9,687,390 B2
(45) Date of Patent: Jun. 27, 2017

(54) PRODUCT TURNER AND PLACER

(71) Applicant: Curt G. Joa, Inc., Sheboygan Falls, WI (US)

(72) Inventors: Benjamin T. Davidson, Howards Grove, WI (US); Sudeep Ingole, Sheboygan, WI (US)

(73) Assignee: Curt G. Joa, Inc., Sheboygan Falls, WI (US)

(*) Notice: Subject to any disclaimer, the term of this patent is extended or adjusted under 35 U.S.C. 154(b) by 0 days.

(21) Appl. No.: 15/005,511

(22) Filed: Jan. 25, 2016

(65) Prior Publication Data

US 2016/0213524 A1 Jul. 28, 2016

Related U.S. Application Data

(60) Provisional application No. 62/107,833, filed on Jan. 26, 2015.

(51) Int. Cl.
*B65G 47/24* (2006.01)
*A61F 13/15* (2006.01)
*B65G 47/252* (2006.01)
*B65G 47/84* (2006.01)

(52) U.S. Cl.
CPC .. *A61F 13/15764* (2013.01); *A61F 13/15723* (2013.01); *B65G 47/252* (2013.01); *B65G 47/843* (2013.01)

(58) Field of Classification Search
CPC ...... A61F 13/15764; B65G 2201/0244; B65G 47/24; B65G 47/847; B65H 2301/33216; B65H 2301/33222; B65H 2406/345; B65H 35/08; B65H 37/04

USPC .......... 198/377.01–377.1, 408, 474.1, 476.1, 198/793, 842, 843, 867.02, 867.03; 271/185; 414/732, 749.4, 758, 779, 795
See application file for complete search history.

(56) References Cited

U.S. PATENT DOCUMENTS

| 3,391,777 | A |   | 7/1968  | Joa |
|-----------|---|---|---------|-----|
| 3,563,377 | A | * | 2/1971  | Southcott ............... B65G 47/24 198/377.04 |
| 3,770,098 | A | * | 11/1973 | Baugnies ................ B29C 49/70 198/377.03 |
| 4,025,373 | A |   | 5/1977  | Hirsch et al. |
| 4,059,187 | A | * | 11/1977 | Rueff ................... B65G 47/843 198/460.1 |
| 4,171,239 | A |   | 10/1979 | Hirsch et al. |
| 4,364,787 | A |   | 12/1982 | Radzins |
| 4,578,133 | A |   | 3/1986  | Oshefsky et al. |

(Continued)

FOREIGN PATENT DOCUMENTS

| CA | 1146129 A1  | 5/1983 |
| CA | 2023816 A1  | 3/1994 |

(Continued)

OTHER PUBLICATIONS

International Search Report pertaining to PCT/US2016/14717, dated Apr. 8, 2016, 7 pages.

*Primary Examiner* — Gregory Adams
(74) *Attorney, Agent, or Firm* — Ryan Kromholz & Manion, S.C.

(57) ABSTRACT

An apparatus is disclosed for severing a continuous web into discrete pieces, and re-orienting the discrete pieces by turning and placing the discrete pieces onto a moving conveyor for further processing as desired.

11 Claims, 4 Drawing Sheets

(56) References Cited

U.S. PATENT DOCUMENTS

| | | |
|---|---|---|
| 4,608,115 A | 8/1986 | Schroth et al. |
| 4,690,050 A * | 9/1987 | Rouly ................. B41F 15/0872 |
| | | 101/35 |
| 5,025,910 A | 6/1991 | Lasure et al. |
| 5,104,116 A | 4/1992 | Pohjola |
| 5,716,478 A | 2/1998 | Boothe et al. |
| 6,116,317 A * | 9/2000 | Tharpe, Jr. ........ A61F 13/15804 |
| | | 156/566 |
| 6,171,049 B1 * | 1/2001 | Wirz ................... H01L 21/6838 |
| | | 198/339.1 |
| 6,482,278 B1 | 11/2002 | McCabe et al. |
| 6,544,375 B1 | 4/2003 | Schmitz |
| 6,604,623 B2 | 8/2003 | Sumi et al. |
| 6,722,494 B2 * | 4/2004 | Nakakado ......... A61F 13/15764 |
| | | 198/377.01 |
| 7,156,219 B2 * | 1/2007 | Voigtmann ............ B29C 31/002 |
| | | 198/377.04 |
| 7,398,870 B2 | 7/2008 | McCabe |
| 7,587,966 B2 | 9/2009 | Nakakado et al. |
| 7,770,712 B2 | 8/2010 | McCabe |
| 7,780,052 B2 | 8/2010 | McCabe |
| 7,975,584 B2 | 7/2011 | McCabe |
| 7,987,964 B2 | 8/2011 | McCabe |
| 7,992,702 B2 * | 8/2011 | Furlotti ................ B65G 47/847 |
| | | 198/377.01 |
| 8,011,493 B2 * | 9/2011 | Giuliani ............... B65G 47/244 |
| | | 198/406 |
| 8,016,972 B2 | 9/2011 | Andrews et al. |
| 8,172,977 B2 | 5/2012 | McCabe et al. |
| 8,293,056 B2 | 10/2012 | McCabe |
| 8,607,959 B2 | 12/2013 | Papsdorf et al. |
| 8,794,115 B2 | 8/2014 | McCabe |
| 8,820,513 B2 | 9/2014 | Papsdorf et al. |
| 8,944,235 B2 | 2/2015 | Papsdorf et al. |
| 9,145,267 B2 | 9/2015 | Yamamoto et al. |
| 9,227,794 B2 | 1/2016 | Papsdorf et al. |
| 2002/0003024 A1 | 1/2002 | Vogt et al. |
| 2005/0230449 A1 | 10/2005 | Meyer et al. |
| 2007/0074983 A1 | 4/2007 | Oh |
| 2007/0193856 A1 | 8/2007 | McCabe |
| 2007/0267149 A1 | 11/2007 | McCabe |
| 2008/0196564 A1 | 8/2008 | McCabe |
| 2008/0276439 A1 | 11/2008 | Andrews et al. |
| 2010/0012458 A1 | 1/2010 | Giuliani et al. |
| 2010/0258240 A1 | 10/2010 | McCabe et al. |
| 2010/0300838 A1 | 12/2010 | McCabe |
| 2010/0327035 A1 | 12/2010 | McCabe |
| 2011/0088233 A1 | 4/2011 | McCabe et al. |
| 2011/0265619 A1 | 11/2011 | McCabe |
| 2012/0186944 A1 | 7/2012 | McCabe |
| 2013/0035222 A1 | 2/2013 | Andrews et al. |
| 2013/0037201 A1 * | 2/2013 | Pagel ................ A61F 13/15723 |
| | | 156/73.1 |
| 2013/0079207 A1 * | 3/2013 | Yamamoto ........ A61F 13/15764 |
| | | 493/379 |
| 2013/0239764 A1 | 9/2013 | McCabe |
| 2013/0239765 A1 | 9/2013 | McCabe et al. |
| 2013/0270065 A1 | 10/2013 | Papsdorf et al. |
| 2013/0270069 A1 | 10/2013 | Papsdorf et al. |
| 2014/0102851 A1 | 4/2014 | Papsdorf et al. |
| 2014/0110226 A1 * | 4/2014 | Findley ............. A61F 13/15764 |
| | | 198/793 |
| 2014/0346010 A1 | 11/2014 | Papsdorf et al. |
| 2016/0074239 A1 | 3/2016 | Papsdorf et al. |

FOREIGN PATENT DOCUMENTS

| | | |
|---|---|---|
| CA | 2573445 A1 | 3/2001 |
| CA | 2559517 A1 | 4/2007 |
| CA | 2754472 A1 | 4/2012 |
| CA | 2781790 A1 | 12/2012 |
| CA | 2792824 A1 | 4/2013 |
| CA | 2870142 A1 | 10/2013 |
| CA | 2870749 A1 | 10/2013 |
| CA | 2814914 A1 | 11/2013 |
| CA | 2815327 A1 | 11/2013 |
| CA | 2631018 A1 | 7/2014 |
| CA | 2652676 A1 | 7/2014 |
| CA | 2622049 A1 | 4/2015 |
| CA | 2699136 A1 | 11/2016 |
| CN | 1917991 A | 7/2009 |
| CN | 104220032 A | 9/2016 |
| CN | 104220033 A | 11/2016 |
| DE | 69006003D1 | 7/1994 |
| DE | 102006047280 A1 | 4/2007 |
| DE | 112013002045 T5 | 1/2015 |
| DK | 2537495 T3 | 8/2015 |
| EP | 47106 A1 | 10/1984 |
| EP | 439897 A1 | 1/1994 |
| EP | 1415628 A1 | 11/2005 |
| EP | 1961403 A2 | 8/2009 |
| EP | 2238955 A1 | 12/2011 |
| EP | 2441419 A1 | 4/2012 |
| EP | 2486903 A2 | 2/2013 |
| EP | 2486904 A2 | 2/2013 |
| EP | 1726414 | 3/2013 |
| EP | 2032338 A2 | 8/2013 |
| EP | 1820757 A1 | 11/2013 |
| EP | 2659868 A1 | 11/2013 |
| EP | 2659869 A1 | 11/2013 |
| EP | 2581068 A2 | 10/2014 |
| EP | 2537495 A2 | 7/2015 |
| EP | 1994919 A1 | 12/2016 |
| ES | 2050380 T3 | 5/1994 |
| ES | 2317760 A1 | 2/2010 |
| ES | 2545365 T3 | 9/2015 |
| FR | 2891811 A1 | 4/2007 |
| GB | 2514986 A | 12/2014 |
| JP | 6023671 A | 11/1985 |
| JP | 61162462 A | 7/1986 |
| JP | 2002530255 A | 9/2002 |
| JP | 200353109 A | 1/2003 |
| JP | 2006230438 A | 9/2006 |
| JP | 2010063716 A | 3/2010 |
| JP | 2015513992 A | 5/2015 |
| JP | 2015513993 A | 5/2015 |
| MX | 2014012416 A | 1/2015 |
| RU | 2014141126 A | 4/2016 |
| SE | 200602047 A | 4/2007 |
| SE | 531151 C2 | 1/2009 |
| WO | WO0100123 A1 | 1/2001 |
| WO | WO2007136813 A2 | 11/2007 |
| WO | WO2013158583 A1 | 10/2013 |
| WO | WO2013158598 A1 | 10/2013 |
| WO | WO 2014/066307 A1 | 5/2014 |

* cited by examiner

PRODUCT TURNER AND PLACER

RELATED APPLICATION

This application claims the benefit of co-pending U.S. Provisional Patent Application Ser. No. 62/107,833, filed 26 Jan. 2015.

BACKGROUND OF THE INVENTION

The invention disclosed herein relates to an apparatus and methods for producing disposable products such as diapers at very high speeds. While the description provided relates to diaper manufacturing, the apparatus and method are easily adaptable to other applications. In particular this invention relates to an apparatus for turning and placing either portions of or discrete disposable products such as diapers.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in continuously fed fashion.

In the creation of a diaper, multiple roll-fed web processes are typically utilized. To create an absorbent insert, the cellulose pulp is unwound from the provided raw material roll and de-bonded by a pulp mill. Discrete pulp cores are created using a vacuum forming assembly and placed on a continuous tissue web. Optionally, super-absorbent powder may be added to the pulp core. The tissue web is wrapped around the pulp core. The wrapped core is debulked by proceeding through a calendar unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition layer web material and a nonwoven web material, both of which are fed from material parent rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a profiled die roller and a smooth platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented, such as disclosed in co-pending U.S. Application No. 61/426,891, owned by the assignee of the present invention and incorporated herein by reference. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slitting is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners. This is also done with turn bars upon entrance to the process.

After the nonwoven web is slit, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

In diapers it is preferable to contain elastics around the leg region in a cuff to contain exudates for securely within the diaper. Typically, strands of elastic are held by a non-woven layer that is folded over itself and contains the elastics within the overlap of the non-woven material. The non-woven is typically folded by use of a plow system which captures the elastics within a pocket, which is then sealed to ensure that the elastics remain in the cuff.

Most products require some longitudinal folding. It can be combined with elastic strands to make a cuff. It can be used to overwrap a stiff edge to soften the feel of the product. It can also be used to convert the final product into a smaller form to improve the packaging.

To assemble the final diaper product, the Insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

Roll-fed web processes typically use splicers and accumulators to assist in providing continuous webs during web processing operations. A first web is fed from a supply wheel (the expiring roll) into the manufacturing process. As the material from the expiring roll is depleted, it is necessary to splice the leading edge of a second web from a standby roll to the first web on the expiring roll in a manner that will not cause interruption of the web supply to a web consuming or utilizing device.

In a splicing system, a web accumulation dancer system may be employed, in which an accumulator collects a substantial length of the first web. By using an accumulator, the material being fed into the process can continue, yet the trailing end of the material can be stopped or slowed for a short time interval so that it can be spliced to leading edge of the new supply roll. The leading portion of the expiring roll remains supplied continuously to the web-utilizing device. The accumulator continues to feed the web utilization process while the expiring roll is stopped and the new web on a standby roll can be spliced to the end of the expiring roll.

In this manner, the device has a constant web supply being paid out from the accumulator, while the stopped web material in the accumulator can be spliced to the standby roll. Examples of web accumulators include that disclosed in U.S. patent application Ser. No. 11/110,616, which is commonly owned by the assignee of the present application, and incorporated herein by reference.

As in many manufacturing operations, waste minimization is a goal in web processing applications, as products having spliced raw materials cannot be sold to consumers. Indeed, due to the rate at which web processing machines run, even minimal waste can cause inefficiencies of scale. In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, the art of web processing would benefit from systems and methods that identify potentially defective product prior to product assembly, thereby eliminating effort during recyclable material harvesting.

Furthermore, to improve quality and production levels by eliminating some potentially defective product, the art of web processing would benefit from systems and methods that ensure higher product yield and less machine downtime.

Some diaper forming techniques are disclosed in co-pending U.S. application Ser. No. 12/925,033 which is incorporated herein by reference. As described therein, a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil.

The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the left side of the product. In this manner, for a single product, one of the two ears will have been rotated 180°.

Ear application to a chassis web can be by a bump method with intermittent adhesive applied to the chassis web, or can be by vacuum transfer.

Two side panel assemblies, including fastening mechanisms, can be attached to two ears, the side panel assemblies attached in a pre-folded condition. Two more ears can coupled to a chassis web to create a front panel to wear about the waist of a user.

Chips of material can also be removed from the ears to provide a diaper with contoured leg openings. In one embodiment, the chips may be removed from the ears before the ears are attached to the chassis web. In an additional embodiment the chips may be removed from the ears after the ears are attached to the chassis web. In an additional embodiment the chips may be removed from the ears and a portion of the chassis web removed after the ears are attached to the chassis web.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion. As in many manufacturing operations, waste minimization is a goal in web processing applications, as products having spliced raw materials cannot be sold to consumers. Indeed, due to the rate at which web processing machines run, even minimal waste can cause inefficiencies of scale.

In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, it is beneficial to use up all of incoming rolls, so that a portion of the incoming rolls do not become waste. That objective is accomplished with the present invention When manufacturing hygiene products, such as baby diapers, adult diapers, disposable undergarments, incontinence devices, sanitary napkins and the like, a common method of applying discrete pieces of one web to another is by use of a slip-and-cut applicator. A slip-and-cut applicator is typically comprised of a cylindrical rotating vacuum anvil, a rotating knife roll, and a transfer device. In typical applications, an incoming web is fed at a relatively low speed along the vacuum face of the rotating anvil, which is moving at a relatively higher surface speed and upon which the incoming web is allowed to "slip". A knife-edge, mounted on the rotating knife roll, cuts a off a segment of the incoming web against the anvil face. This knife-edge is preferably moving at a surface velocity similar to that of the anvil's surface. Once cut, the web segment is held by vacuum drawn through holes on the anvil's face as it is carried at the anvil's speed downstream to the transfer point where the web segment is transferred to the traveling web.

Continual improvements and competitive pressures have incrementally increased the operational speeds of disposable diaper converters. As speeds increased, the mechanical integrity and operational capabilities of the applicators had to be improved accordingly.

In some instances, disposable products manufacturers choose to use pre-formed stretched laminate to construct products such as diapers. In a typical diaper, it is preferred to have a stretch from side to side across the waist of a user. In prior art diaper construction techniques, machines are used that construct stretch laminates in a machine direction, and then rotate the stretch laminates to receive an absorbent core roughly perpendicular to the front and rear panels. However, if the pre-formed stretched laminate is supplied with the stretch perpendicularly to the unwind or machine direction, the prior art machines would not orient the stretch characteristics of the front and rear or back panels properly. Therefore, a machine is necessary to fabricate diapers from an unwind roll that presents the stretch direction perpendicular to the machine direction.

SUMMARY OF THE INVENTION

A core forming unit feeds a core to a cutting unit, where a core is wrapped with a core topsheet and backsheet. The core insert is folded and a front wing web and a back wing web are coupled to the folded core. If a pant type diaper is desired, side seams of the front wing web and back wing web are bonded together at side seam regions. Disclosed in this application are methods and apparatus for severing a continuous web, such as but not limited to a continuous web of formed and seamed pant-type diaper products, into discrete pieces, and re-orienting the discrete pieces by turning and placing the discrete pieces. Next, portions of the front wing web and back wing web are folded over to create a compact product for packaging and shipment.

A method of processing a continuous web is disclosed, the method comprising providing an incoming continuous web of material at a first orientation relative to horizontal, severing the web into discrete pieces, each piece comprising a leading edge, a trailing edge, a top edge and a bottom edge, acquiring a discrete piece with a rotating and pivoting unit, rotating said discrete piece about an axis of the first orientation, spacing adjacent pieces by separating a trailing edge of a first discrete piece from a leading edge of a second discrete piece, reorienting said discrete pieces from said first orientation relative to horizontal to a second orientation relative to horizontal, depositing said pieces and spacing adjacent pieces by separating a top edge of said first discrete piece from a bottom edge of said second discrete piece.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

In traditional diaper manufacturing techniques, a stretch laminate is formed by laying down elastic sheets or strands in a machine direction. This laminate is then re-oriented to receive an absorbent core also running and applied in the machine direction. In the present case, a pre-made unidirectional stretch material can be employed (or the stretch laminate is formed upstream) and the direction of stretch is in the cross machine direction during the manufacturing process.

Figure 1:
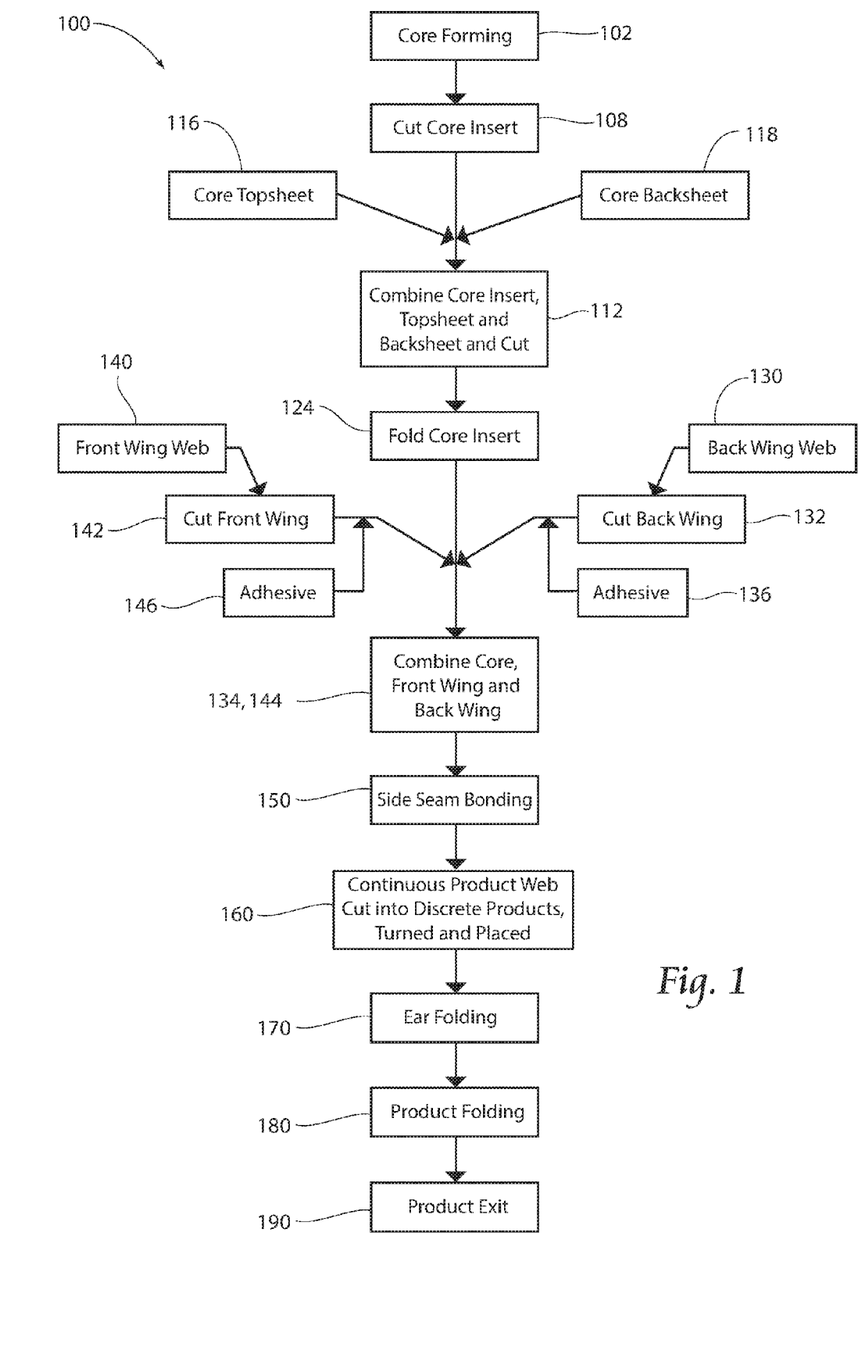
FIG. 1 is a schematic of a representative web processing system.

Referring to FIG. 1, a schematic representation of the present methods and machinery is shown. First, a core forming procedure takes place at core forming unit 102. A continuous core is cut into individual core portions at core cutter 108, and the cut core is wrapped by placing a topsheet 116 and a backsheet 118 about the cut core. It is noted that the core could remain continuous and cut individually after receiving a wrap such as with topsheet 116 and backsheet 118.

Next, the core is folded by a folder 124 such as a tucker blade. The folded core is introduced into a combining unit where the folded core receives on one side a front wing web 140, which has been pre-cut and applied with adhesive for bonding with the folded core. The folded core receives on the other side a back wing web 130, which has also been pre-cut and applied with adhesive for bonding with the folded core.

The core, front wing and back wing combination is passed to a side seam bonding unit 150, such as an ultrasonic bonding unit, where the front wing and back wing are bonded together at side seam regions. At this point the diaper is fully formed, but in a continuous web.

The present application is primarily directed at station 160, which is an apparatus for severing a continuous web of fully formed diapers into discrete diapers, and re-orienting the discrete diapers by turning and placing the discrete diapers. It is noted that the apparatus of the present invention can also be used for cutting, turning, and otherwise re-orienting continuous webs of materials other than a continuous web of fully formed diapers.

For ease of packaging and shipping, portions of the front wing and back wing which extend widthwise outwardly of the folded core can be folded over the folded core, for instance using a canoe folder by folding unit 170. If desired, the product can then be folded in half again for compact packaging by folding unit 180. The product is then passed on at the product exit 190 for further processing as desired.

Figure 2:
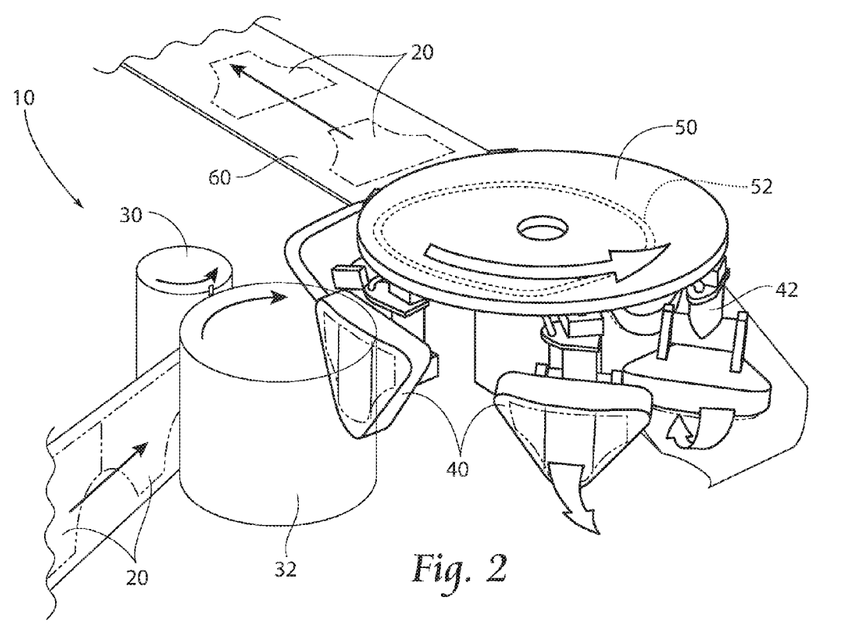
FIG. 2 is a perspective view of a machine for severing a continuous web into discrete pieces and re-orienting the discrete pieces by turning and placing the discrete pieces.

Referring now to FIG. 2, an incoming web such as a web of continuous formed and sideseam bonded pants type paper products 20 is shown entering a vertically oriented knife 30 and anvil 32 arrangement. Anvil 32 carries discrete pants type diapers 20 about the anvil 32 to a puck 40, which acquires the pant type diaper 20 from the anvil 32 at an acquisition point. A series of pucks 40 are rotatably mounted, carried, and rotated by a rotating unit 50. The pucks 40 acquire the individual pant type diapers 20 in a vertical orientation and, as shown, the pucks 40 rotate in a counterclockwise direction. As the pucks 40 rotate in the counter clockwise direction, pucks 40 also pivot downwardly, to transition the pant type diaper 20 from a vertical orientation to a horizontal orientation. The pucks 40 are preferably vacuum pucks to retain the pant-type diapers 20 upon a carrying surface of the pucks 40. However, other attraction or retaining forces can be employed to retain the pant-type diapers 20 on the carrying surface of the pucks 40. The pucks 40 release individual pant type diapers 20 onto a conveyor 60, at a deposition point. In this manner a continuous web of formed pant-type diapers is separated into discrete pant-type diapers 20 and re-oriented from a vertical orientation entering anvil 32/knife 30 combination to a horizontal orientation when carried by conveyor 60.

Continuing their revolution, pucks 40 pivot from their horizontal orientation at the deposition point of the individual pant-type diapers 20 onto the conveyor 60, to their original vertical orientation upon returning to the acquisition point proximal to anvil 32.

Instead of, or in addition to depositing the pant-type diapers 20 onto a conveyor 60, in an alternative embodiment of the present invention, the unit shown in FIG. 2 can be used to space and reposition other discrete pieces in addition to individually cut pant-type diapers 20. For instance, the turner/placer of FIG. 2 can be used to turn and space other discrete elements of disposable products, such as ear webs, side panel webs, waist band features, or any other discrete object. Instead of depositing discrete pieces 20 onto a conveyor 60, a running web of material can take the place of the conveyor 60, and a bonding unit can be used to bond discrete pieces coming from the product turner/placer onto the running web of material. In this manner, the discrete pieces can be placed at one or more outboard edges of the running web (for instance if ears or side panels are desired to be place), or within the cross-machine direction width of the running web (for instance a desirable placement of an absorbent core, to turn, place, and space adjacent cores onto a running web).

Figure 3:
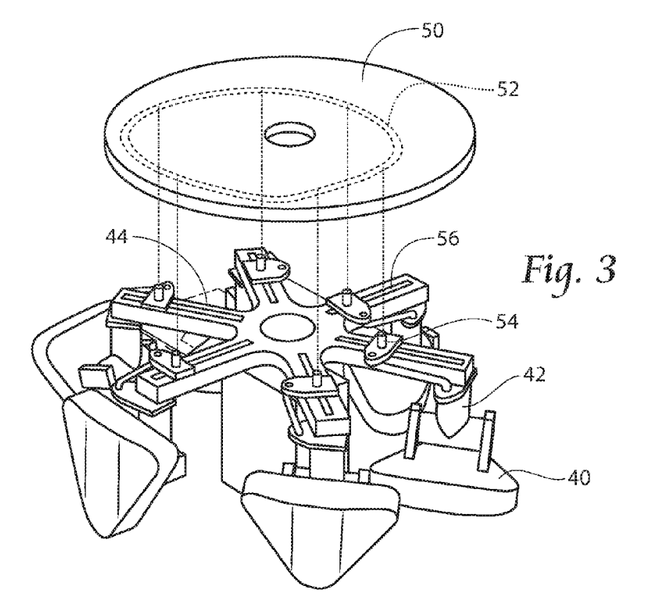
FIG. 3 is an exploded view of portions of the machine of FIG. 2.

Referring now to FIG. 3, pucks 40 are carried by pivoting member 42 which pivots pucks 40 from vertical to horizontal orientations. Pivoting members 42 are carried by arms 44 extending radio Lee from an axis about which the pucks 40 can rotate. Also carried on arms 44 are slots 56 for slidably receiving cam followers 54, which control the radial position of the pucks 40. Cam followers 50 are operably engaged with cam slot 52, which is an eccentric shape disposed on frame member 50. As the pucks 40 rotate, cam follower 54 travels through the eccentric 52 and adjusts the lateral position of the pucks 40, as desired. In this manner, the relative rotational speed of the pucks 40 can be changed.

Figure 4:
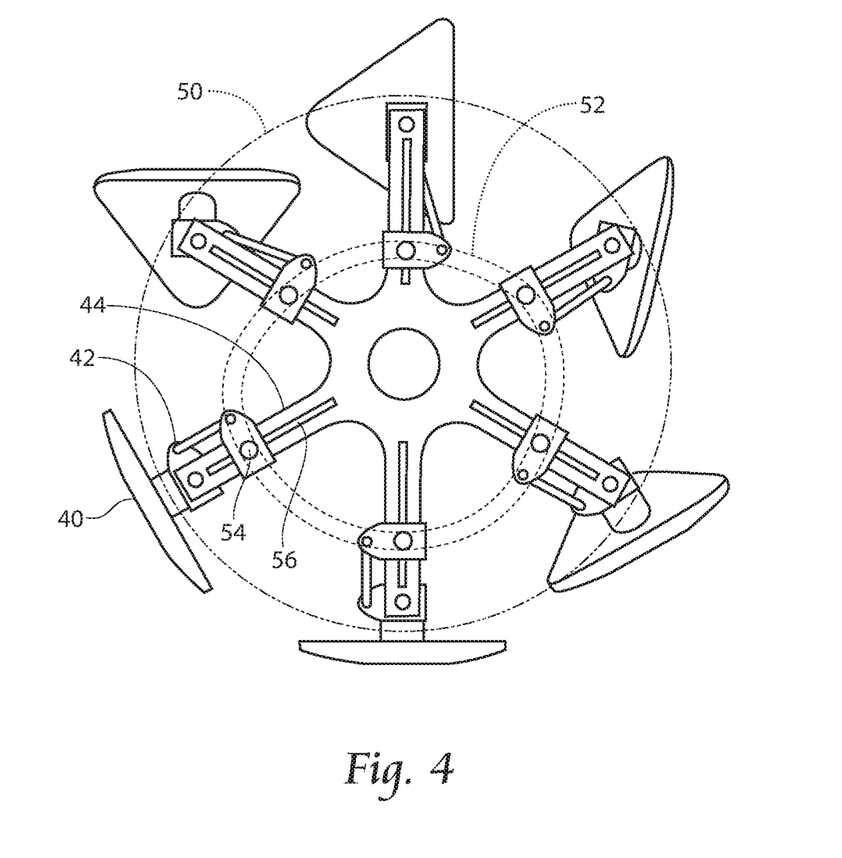
FIG. 4 is a top view of portions of the machine of FIG. 2.

Referring now to FIG. 4, it is seen that the cam followers 54 travel throughout the eccentric channel 52 provided on body 50. During rotation, the pucks 40 pivot from a vertical orientation as seen at the bottom of FIG. 4, to a horizontal orientation pictured at the top of FIG. 4, and then the pucks 40 pivot back from the horizontal to the vertical orientation throughout rotation.

Figure 5A:
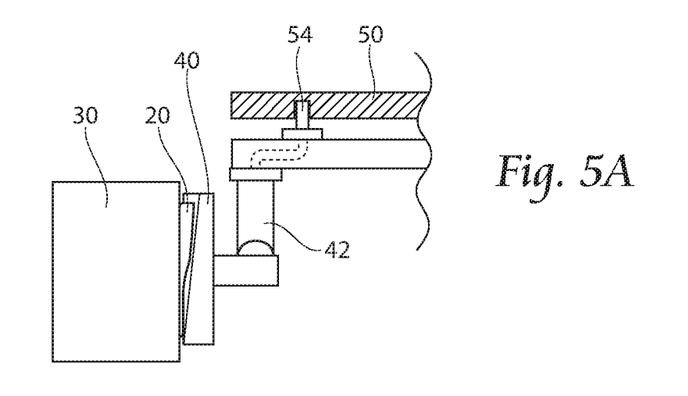
FIGS. 5a-5d are a sequential series of side views of a rotating puck of the present invention picking up discrete pieces from an anvil roll at an acquisition point and rotating and pivoting the puck to a deposition point.
Figure 5B:
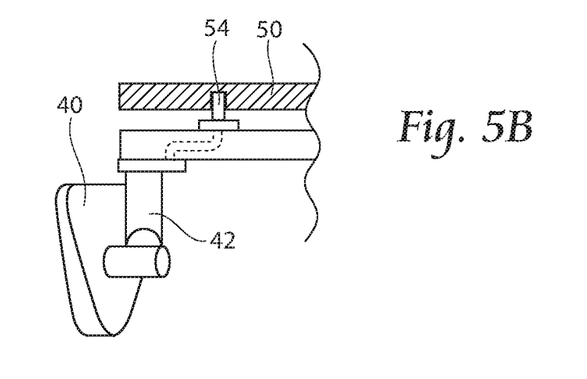
Figure 5C:
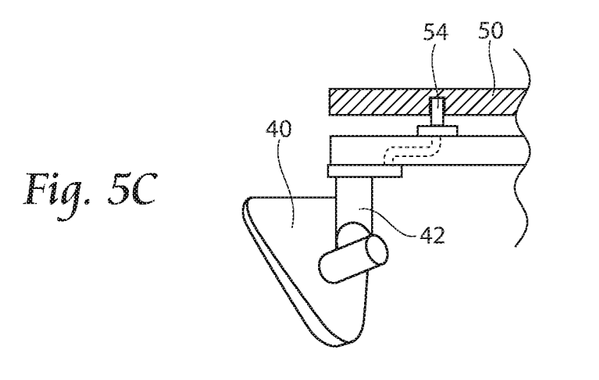
Figure 5D:
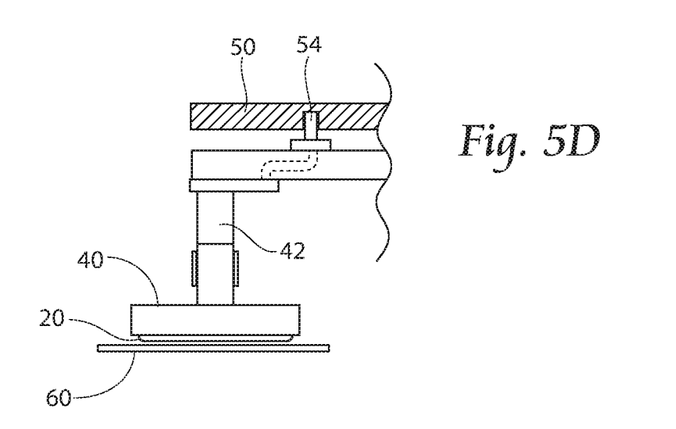

Referring now to FIG. 5A, a side view of a puck 40 is shown acquiring a discrete paper product 20 from a vertically oriented anvil drum 30, at an acquisition point. In FIG. 5B, the puck 40 has begun to rotate away from the acquisition point. As shown in figure SC as the puck 40 continues to rotate, the puck 40 begins to pivot operation of by pivoting member 42, from a vertical towards a horizontal orientation. Referring to FIG. 5D the puck 40 has now pivoted to a horizontal position and, at a deposition point, is in position to lay down a discrete diaper 20 onto a conveyor 60.

After the discrete diaper products 20 are placed onto conveyor 60, as mentioned in FIG. 1, the discrete products 20 can be passed downstream for ear and product folding stations 170 and 180, if desired.

Those skilled in the art will recognize that the present configuration allows for easy size change operations. In a size change operation, machines are reconfigured to handle discrete portions of a web, such as diapers 20, of variable sizes for example from small to large. In order to configure the machine of FIG. 2 for a size change, it may be necessary to adjust the position of the conveyor 60, upwardly or downwardly. Alternatively, one could adjust the position of the pucks 40, also upwardly or downward and inwardly or outwardly, to receive larger or smaller discrete web portions.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of processing a continuous web; the method comprising:
   providing an incoming continuous web of material comprising a first edge and a second edge, said continuous web of material provided along a first plane of travel defined by said first and said second edges;
   severing the web into discrete pieces;
   acquiring a discrete piece with a rotating and pivoting unit;
   rotating said discrete piece about an axis of rotation of said rotating and pivoting unit;
   pivoting said discrete piece to a second plane of travel, said second plane of travel intersecting said axis of rotation of said rotating and pivoting unit;
   said rotating and pivoting steps reorienting said discrete pieces from said first plane of travel to said second plane of travel, said second plane of travel intersecting said first plane of travel;
   depositing said pieces along said second plane of travel and spacing adjacent pieces by separating a top edge of said first discrete piece from a bottom edge of said second discrete piece.

2. A method according to claim 1, wherein said first plane of travel is vertical.

3. A method according to claim 1, wherein said first plane of travel is horizontal.

4. A method of claim 1, said pieces deposited onto a conveyor.

5. A method of claim 1, said pieces deposited onto a running web of material.

6. A method of claim 1, said pieces comprising a diaper.

7. A method of processing a continuous web; the method comprising:
   acquiring a rotating and pivoting unit series of discrete pieces comprising a leading edge, a trailing edge, a top edge and a bottom edge, said pieces traveling at a first orientation relative to horizontal;
   rotating said discrete pieces about an axis the first orientation;
   pivoting said discrete nieces about a pivot axis;

spacing adjacent pieces by separating a trailing edge of a first discrete piece from leading edge of a second discrete piece;

reorienting said discrete pieces from said first orientation relative to horizontal to a second orientation relative to horizontal parallel with said pivot axis;

depositing said pieces and spacing adjacent pieces by separating a top edge of said first discrete piece from a bottom edge of said second discrete piece.

8. A method according to claim 7, wherein said first orientation relative to horizontal is vertical.

9. A method according to claim 7, therein said second orientation relative to horizontal is horizontal.

10. A method of claim 7, said pieces deposited onto a conveyor.

11. A method of claim 7, said pieces deposited onto a running web of material.

\* \* \* \* \*